United States Patent [19]

Henery et al.

[11] 4,172,961

[45] Oct. 30, 1979

[54] PRODUCTION OF 1,4-BUTANEDIOL

[75] Inventors: James D. Henery, Houston; Robert P. Arganbright, Seabrook, both of Tex.

[73] Assignee: Denka Chemical Corporation, Houston, Tex.

[21] Appl. No.: 602,992

[22] Filed: Aug. 8, 1975

[51] Int. Cl.$^2$ .............................................. C07C 31/20
[52] U.S. Cl. .................................... 568/864; 568/885
[58] Field of Search .......... 260/635 D, 637 R, 635 E, 260/643 D; 568/864

[56] References Cited

U.S. PATENT DOCUMENTS

| | | | |
|---|---|---|---|
| 2,091,800 | 8/1937 | Adkins et al. | 260/635 D |
| 3,083,236 | 3/1963 | Utne et al. | 260/635 E |
| 3,088,982 | 5/1963 | Feldman et al. | 260/643 D |
| 3,268,588 | 8/1966 | Horlenko et al. | 260/635 D |
| 3,478,103 | 11/1969 | Hann | 260/635 D |
| 3,917,720 | 11/1975 | Webb et al. | 260/637 R |

*Primary Examiner*—Joseph E. Evans
*Attorney, Agent, or Firm*—Kenneth H. Johnson

[57] ABSTRACT

An improved process for the production of 1,4-butanediol is disclosed wherein a dialkyl alkoxy succinate-containing mixture is contacted with hydrogen at elevated temperature and pressure in the presence of a copper chromite hydrogenation catalyst to form a mixture comprising 1,4-butanediol and the corresponding alkanol. In a preferred embodiment, dibutyl butoxy succinate is converted to 1,4-butanediol and n-butanol at high selectivities.

5 Claims, 1 Drawing Figure

PRODUCTION OF 1,4-BUTANEDIOL

BACKGROUND OF THE INVENTION

1. Field of the Invention

This invention relates to an improved method for the production of 1,4-butanediol. More particularly, this invention relates to a method for concurrently preparing 1,4-butanediol and a monohydric alcohol in a catalyzed reduction of certain dialkyl alkoxy succinate-containing mixtures.

2. Description of the Prior Art 1,4-Butanediol is a monomer used in the production of polybutylene terephthalate, a unique engineering plastic. Butanediol has been manufactured commercially by processes involving the Reppe reaction of acetylene and formaldehyde followed by hydrogenation of the reaction mixture. Other processes for the production of 1,4-butanediol involve the hydrolysis of dichlorobutanes or the hydrogenation of maleic anhydride.

It is an object of the instant invention to provide a process for the conversion of dialkyl alkoxy succinate-containing mixtures into 1,4-butanediol and the corresponding alkanol(s), both of which are important chemicals commercially.

SUMMARY OF THE INVENTION

In accordance with the instant invention dialkyl alkoxy succinate-containing mixtures are intimately contacted with hydrogen at elevated temperature and pressure in the presence of a copper chromite hydrogenation catalyst to form a reaction mixture comprising 1,4-butanediol and monohydric alcohol. The process of this invention is carried out at a temperature of from about 200° C. to about 300° C. and at a hydrogen pressure of from about 2,000 psig to about 4,000 psig to produce the 1,4-butanediol at high conversion levels and high selectivities based upon the dialkyl alkoxy succinate starting material.

BRIEF DESCRIPTION OF THE FIGURE

The invention will be illustrated by reference to the attached FIGURE which represents a schematic flow diagram of a preferred embodiment of this invention.

DESCRIPTION OF THE PREFERRED EMBODIMENTS

In accordance with the present invention, dialkyl alkoxy succinates of the structure wherein R, R′ and R″, independently, are alkyl of from 2 to about 10 carbon atoms, and preferably alkyl of from about 4 to about 6 carbon atoms, are converted to a mixture comprising 1,4-butanediol and the corresponding monohydric alcohols (R-OH, R′-OH, and R″-OH). The reaction is effected by contacting the above-described dialkyl alkoxy succinates with hydrogen at elevated temperature and pressure in the presence of a copper chromite hydrogenation catalyst. Especially preferred in the practice of this invention are dialkyl alkoxy succinates of the above formula wherein R, R′ and R″ are the same thereby producing a reaction product comprising 1,4-butanediol and one alkanol as the major products. An example of an especially preferred dialkyl alkoxy succinate is dibutyl butoxy succinate.

The dialkyl alkoxy succinates which are employed in practicing the present invention are known compositions of matter and can be prepared by the acid-catalyzed reaction of alkanols with fumaric acid as is taught in U.S. Pat. No. 2,894,980. Such dialkyl alkoxy succinates can also be obtained as co-products in conventional processes for the acid catalyzed production of dialkyl esters from maleic acid and fumaric acid.

Still another source of dialkyl alkoxy succinates which may be employed in practicing the process of this invention includes a non-catalyzed high temperature esterification-dehydration process wherein maleic acid and/or fumaric acid are reacted with certain monohydric alcohols or mixtures thereof. In this process the monohydric alcohol is both an esterification agent and a dehydrating agent and is selected for its ability to form an azeotrope with water thereby to facilitate the removal of water from the reaction zone.

The monohydric alcohols which are suitable in the practice of such esterification processes include monohydric alcohols having from 2 to about 10 carbon atoms. Preferred monohydric alcohols are those which form a heterogeneous azeotrope with water. Such heterogeneous azeotropic compositions upon condensing form two immiscible phases, an alcohol-rich phase and a water-rich phase. Monohydric alcohols which form heterogeneous azeotropes with water include n-butanol, isoamyl alcohol, and tertiary amyl alcohol. Especially preferred in the practice of this invention is n-butanol.

The maleic acid or fumaric acid-containing feedstocks which are employed in the non-catalytic process for production of dialkyl alkoxy succinates can be commercially available maleic acid, maleic anhydride or fumaric acid. However, also suitable are aqueous maleic acid solutions having from about 10 to about 60 wt.% maleic acid, and preferably from about 30 to about 50 wt.% maleic acid, and may contain other impurities commonly associated with the production of maleic acid. For example, a typical feedstock is the maleic acid scrubber water solution obtained as an intermediate in a commercial process for the production of maleic acid by the air oxidation of a hydrocarbon, e.g., benzene. Such maleic acid scrubber solutions generally contain a small proportion of fumaric acid, an isomer of maleic acid, formaldehyde and a small proportion of other water soluble by-products from the oxidation reaction in which the maleic acid was produced. Examples of such impurities include aliphatic monocarboxylic acids having from about 2 to about 6 carbon atoms and aliphatic aldehydes having from about 2 to about 6 carbon atoms.

Other sources from which fumaric acid is available other than that contained in the maleic acid scrubber solution, includes, for example, the fumaric acid which accumulates as a solid phase in storage tanks, in the commercial production of maleic anhydride. This solid fumaric acid may be recovered from the storage tanks, and employed in preparing the dialkyl alkoxy succinates which are employed in the process of this invention. Still another source of feedstock for the production of the dialkyl alkoxy succinates is the distillation column bottoms from the final distillation of maleic anhydride, which bottom stream consists essentially of fumaric acid and maleic anhydride employed in preparing the succinate esters.

The aqueous maleic acid and/or fumaric acid-containing solution is introduced into an intermediate portion of a distillation zone wherein it is distilled in the presence of the monohydric alcohol hereinbefore described. The alcohol serves both as a dehydrating agent and an esterification agent in forming the dialkyl alkoxy succinates which are the subject of this invention. The alcohol is generally introduced into the distillation zone at a point near the top of the zone and the dialkyl alkoxy succinate-containing product is recovered from the distillation zone as a bottoms product. The dialkyl maleates and dialkyl fumarates which can be present in the bottom product represent intermediates in the esterification of maleic acid and fumaric acid to dialkyl alkoxy succinate. The intermediates may be recycled for further reaction to the desired product. The water contained in the aqueous maleic acid-containing feedstock and that formed as a result of the esterification reaction are removed in an overhead vapor product from the distillation zone. The composition of the overhead vapor product will depend upon the choice of monohydric alcohol selected, but in any case the water is distilled from the distillation zone as an azeotrope in combination with the dehydrating agent. The dehydrating agent is generally recovered from this azeotropic composition, as will be hereinafter explained, and is returned to the distillation zone for reuse.

The overhead pressure of the distillation zone is selected such that the temperature in the lower portion of the distillation zone is high enough to enable the formation of the dialkyl alkoxy succinate. Moreover, the distillation column must be sufficiently efficient such that the lower portion of the distillation zone is substantially free of water. By substantially free of water is meant that any free water contained in the aqueous maleic acid-containing feedstock has been distilled out of the mixture at a point in the distillation zone above this lower portion of the zone and that the small amounts of water which are formed as the esterification reaction occurs in this lower portion of the distillation zone are quickly distilled upwards from that portion of the zone. Thus, the amount of water present in the lower portion of the distillation zone where the bulk of the esterification reaction occurs, is very low and gets progressively less towards the bottom of the distillation zone at which point the esterification of the maleic acid and fumaric acid has been substantially completed.

The pressure which must be established in the distillation zone in order to produce the temperature necessary to effect the formation of the dialkyl alkoxy succinate will depend, of course, upon the choice of esterification agent. The necessary operating pressure will be highest whenever the esterification agent is ethanol and will decrease as the molecular weight of the monohydric alcohol increases. In a preferred embodiment of the process of this invention, employing n-butanol as the esterification agent, a pressure of from about 50 to about 100 psig is employed in order to maintain the temperature in the lower portion of the distillation zone at a temperature in the range of from about 190° C. to about 275° C. with a temperature in the range of from about 220° C. to about 260° C. being preferred. At temperatures below about 190° C. there is only a very small proportion of the dibutyl butoxy succinate formed. By lower portion of the distillation zone is meant that portion which provides sufficient residence time in the zone at the aforementioned desired conditions to ensure substantial conversion of the maleic acid and fumaric acid to the corresponding dialkyl alkoxy succinate. Generally, this represents approximately the lower one-third of the distillation zone although a greater proportion of the zone may be required for some embodiments of this invention. At any rate, that portion of the zone in which the maleic acid and fumaric acid need to be in contact with the monohydric alcohol in the substantial absence of free water to effect esterification to the corresponding dialkyl alkoxy succinate, can be readily determined empirically without undue experimentation as will be apparent to one skilled in the art.

As previously mentioned, the overhead vapor product from the distillation zone comprises water and the monohydric alcohol in an azeotropic composition. It is desirable to recover the monohydric alcohol from the azeotropic mixture and return it to the distillation zone as a reflux. However, the manner in which the monohydric alcohol is recovered from the azeotropic composition will depend upon whether the azeotrope recovered from the distillation zone is a heterogeneous azeotrope or a homogeneous azeotrope. Some monohydric alcohols, such as ethanol and n-propanol, for example, form a minimum boiling azeotropic mixture with water, which upon condensation exist as a single homogeneous liquid phase. By contrast, monohydric alcohols such as n-butanol and isoamyl alcohol, for example, form an azeotropic composition with water, which upon condensation separates into two immiscible liquid phases: an alcohol-rich phase and a water-rich phase. The relative proportions of alcohol and water in each of the two immiscible phases will depend upon the temperature at which the azeotropic mixture is condensed. It is preferred that a monohydric alcohol that forms a heterogeneous azeotrope with water be employed in preparing the dialkyl alkoxy succinate of this invention. In such a process the alcohol-rich phase which is obtained upon condensation of the overhead product from the esterification zone has an alcohol concentration greater than the alcohol concentration in the azeotropic overhead product. Distillation of this alcohol-rich phase produces an overhead vapor product in which the alcohol and water are present in the azeotropic proportions and a bottoms product which is substantially anhydrous monohydric alcohol. This bottoms product is recycled to the esterification-dehydration zone for reuse in the esterification-dehydration process.

The water-rich phase which is obtained upon condensation of the overhead product from the esterification-dehydration zone has a water concentration which is greater than the water concentration in the azeotropic overhead product. Distillation of the water-rich phase produces an overhead vapor product in which the alcohol and water are present in azeotropic proportions and a bottoms product which is substantially water. The overhead vapor azeotropic products obtained from each of the aforementioned distillations are combined with the overhead vapor product from the esterification-dehydration zone. In this manner, substantially all of the contained monohydric alcohol is recovered in the process.

Whenever a monohydric alcohol that forms a homogeneous azeotrope with water is employed in preparing the dialkyl alkoxy succinates, it is necessary to add a third component to the condensed overhead in order to recover the monohydric alcohol. This third component is selected for its ability to form a heterogeneous ternary azeotrope with the alcohol-water mixture. Examples of suitable third components include benzene and toluene.

In such a ternary system, the overhead product from the esterification-dehydration zone is combined with the third component and is subjected to a first distillation. The bottoms product from this first distillation comprises substantially the monohydric alcohol and is recycled to the esterification-dehydration zone. A side draw obtained from a lower portion of the first distillation column comprising the third component as a major constituent and a minor amount of the monohydric alcohol is recycled for combination with the feed to the first distillation column.

The overhead product from the first distillation column is a ternary azeotrope, which upon condensation separates into two immiscible layers. The lower layer is a water-rich layer additionally containing minor proportions of monohydric alcohol and the third component. The upper layer is rich in the third component with minor proportions of the monohydric alcohol and water.

This upper layer is recycled and combined with the overhead product from the esterification-dehydration zone. The lower water-rich layer is subjected to a distillation in which water is recovered as a bottoms product and a ternary azeotrope is recovered as the overhead product. This overhead product is combined with the ternary azeotrope recovered as the overhead product from the first distillation. In this manner, substantially all of the monohydric alcohol and third component are recovered.

The crude dialkyl alkoxy succinate product obtained as the bottoms product from the esterification-dehydration zone additionally comprises dialkyl maleate, dialkyl fumarate and monohydric alcohol. The dialkyl esters of maleic and fumaric acid represent intermediates in the esterification of maleic and fumaric acid. These intermediates can be recovered and recycled for further esterification to dialkyl alkoxy succinates. Generally, the acid number of the bottoms product from this esterification-dehydration zone is less than 1.0 mg KOH/g with an acid number of approximately 0.2 mg KOH/g or less being typical.

According to the process of this invention, the dialkyl alkoxy succinate-containing feedstock is contacted at elevated temperature and pressure with hydrogen in the presence of a copper chromite hydrogenation catalyst. The reaction products formed from this hydrogenation reaction are 1,4-butanediol and monohydric alcohol (if both alkyl groups and the alkyl moiety of the alkoxy group are the same). If the alkyl groups and the alkyl moeity of the alkoxy group are dissimilar, there will result a mixture of monohydric alcohols, corresponding to these alkyl constituents. Any maleic and fumaric unsaturation present (the aforementioned dialkyl esters of maleic and/or fumaric acid) is also hydrogenated resulting in the formation of additional 1,4-butanediol and minor proportions of an intermediate—the corresponding dialkyl succinate esters.

Stoichiometrically, five moles of hydrogen are required for each mole of dialkyl alkoxy succinate converted to butanediol. However, the hydrogenation reaction is generally carried out in the presence of excess hydrogen. The reaction is carried out under a hydrogen pressue of from about 2,000 psig to about 4,000 psig with a hydrogen pressure of from about 2,500 psig to about 3,500 psig being preferred. The hydrogen may be present as hydrogen or as a hydrogen-containing gas in which the hydrogen is admixed with a gas inert in this reaction environment.

The hydrogenation catalyst employed in the process of this invention is generally referred to as a copper chromite hydrogenation catalyst. However, as will be apparent to one skilled in the art, the term copper chromite is commonly used to refer to mixtures of oxides of copper and chromium, for example, a mixture of cupric oxide and chromic oxide. It is also well-known in the art that such copper chromite hydrogenation catalyst can additionally include other metals or metal oxides as promoters. For example, barium promoted copper chromite catalysts are commonly available.

The form in which the copper chromite catalyst is employed is not critical to the process of this invention. The catalyst is generally employed in a finely subdivided form but may also be employed as particles or chunks of larger size. Generally, the copper chromite catalyst is employed in an amount of from about 2.0 to about 20.0 wt.%, based upon the amount of dialkyl alkoxy succinate present in the feedstock, with an amount of from about 3.0 to about 10.0 wt.% on the same basis being preferred. The temperature at which the hydrogenation reaction is carried out is generally in the range of from about 200° C. to about 300° C., with a temperature of from about 220° C. to about 280° C. being preferred.

In an embodiment of this invention wherein the copper chromite hydrogenation catalyst is employed in the form of a finely divided powder, it is desirable that the reaction mixture be subjected to vigorous agitation in order to ensure efficiency of the hydrogenation reaction and maintain a high selectivity for the formation of the desired products.

The residence time of the dialkyl alkoxy succinate-containing feedstock in the hydrogenation zone will depend of course upon the catalyst concentration and the particular reaction conditions employed. Generally, in batch processes wherein the copper chromite hydrogenation catalyst is employed as a slurry in an amount hereinbefore described, residence times of from about 10 minutes to about 120 minutes in the hydrogenation zone are satisfactory, with a residence time of from about 30 minutes to about 90 minutes in the hydrogenation zone being preferred.

Although not required in the hydrogenation process herein described, a solvent can be employed in the hydrogenation process. A suitable solvent is the monohydric alcohol employed in preparing the dialkyl alkoxy succinate feedstock. Thus, in one embodiment of this invention, a crude dialkyl alkoxy succinate-containing product from that zone is employed directly in the hydrogenation zone without removal of the monohydric alcohol contained in that crude product. Other suitable solvents include p-dioxane, tetrahydrofuran, and the like.

The crude 1,4-butanediol-containing product obtained from the hydrogenation zone comprises, in addition to 1,4-butanediol and the monohydric alcohol(s) obtained from the hydrogenation reaction, other impurities formed as by-products in the hydrogenation reaction. Illustrative of these impurities, when dibutyl butoxy succinate is employed as the dialkyl alkoxy succinate in the process of this invention, are dibutyl succinate, dibutyl fumarate, $\gamma$-butyrolactone, 2-butoxy-1,4-butanediol and other higher molecular weight high boiling residues. In addition, the crude 1,4-butanediolcontaining product will contain excess hydrogen, the copper chromite hydrogenation catalyst and a small proportion of light ends, generally including the formal of the monohydric alcohol employed in the esterification-dehydration reaction, e.g., dibutylformal.

The excess hydrogen is recovered from the crude 1,4-butanediol-containing mixture and is recycled for use in the hydrogenation zone. In batch processes wherein the crude 1,4-butanediol-containing mixture additionally contains the copper chromite hydrogenation catalyst in a finely divided form, the catalyst is recovered from the reaction mixture by conventional means, e.g., filtration, centrifugation and the like. The recovered copper chromite hydrogenation catalyst can be recycled to the hydrogenation zone. It is generally desirable to take a portion of the recovered catalyst and subject it to a regeneration process in order to maintain the catalyst system at a desired level of activity. Such regeneration methods are well-known in the art. Whenever the copper chromite catalyst is recovered and recycled for reuse as described herein, it is equivalently useful to add a small amount of fresh catalyst to maintain the desired level of activity.

The crude 1,4-butanediol-containing mixture which has been freed of excess hydrogen and hydrogenation catalyst is generally introduced to a light ends distillation zone wherein the monohydric alcohol(s) and other volatile light ends materials are recovered as on overhead vapor product. An advantage of the process of this invention is that the monohydric alcohol(s) which may be recovered from this overhead product are commercially important and valuable co-products and are produced in substantial quantities.

The bottoms product from the light ends recovery zone comprises the 1,4-butanediol in admixture with a number of other reaction products from the hydrogenation of the dialkyl alkoxy succinate from which it was derived. For example, whenever dibutyl butoxy succinate is employed in practicing the process of this invention, the following compounds are generally found in such crude 1,4-butanediol reaction product in the following approximate concentrations:

| | |
|---|---|
| dibutyl succinate | 2.0–5.0 mole % |
| dibutyl butoxy succinate | 1.0–3.0 mole % |
| γ-butyrolactone | 1.0–3.0 mole % |
| γ-hydroxybutyraldehyde | 1.0 mole % |
| 2-Butoxy-1,4-butanediol | 2.0–4.0 mole % |
| High boiling residues | 4.0–8.0 wt. % |

In addition to the above impurities, there may be a considerable quantity of n-butanol present if the crude 1,4-butanediol-containing mixture, is not subjected to an efficient light ends distillation, as hereinbefore described. It will be apparent to one skilled in the art, that the foregoing description of the impurities present in a crude 1,4-butanediol-containing mixture relate to butyl derivatives, which merely reflects the choice of dialkyl alkoxy succinate employed in the process of this invention.

The 1,4-butanediol is recovered from the crude 1,4-butanediol-containing mixture by conventional techniques, e.g., distillation and the like. However, in a preferred embodiment of this invention, 1,4-butanediol is recovered in high purity in a novel multistep extraction-distillation process which is more fully described in co-pending application Ser. No. 602,986, filed of even date with this application and now U.S. Pat. No. 4,032,583. The multistep process for the recovery of 1,4-butanediol involves the extraction of the aforementioned impurities from an aqueous mixture of the crude 1,4-butanediol and thereafter recovering the 1,4-butanediol in a distillation carried out at reduced pressure.

Initially, the crude 1,4-butanediol-containing mixture is diluted with water to form an aqueous mixture having a water content of from about 5 to about 75 wt.% water, and preferably from about 20 to about 50 wt.%. It has been found that by adding water to the crude butanediol-containing mixture improves the phase separation obtained between the aqueous phase and the hydrocarbon extract phase in the extraction zone. Moreover, maintaining a water concentration within the aforementioned range results in an improved extraction of impurities into the hydrocarbon extract phase.

In the extraction zone, the aqueous 1,4-butanediol-containing mixture is contacted with a hydrocarbon extracting agent which is immiscible with the aqueous butanediol-containing mixture. Suitable hydrocarbon extracting agents which may be employed include alkanes having from about 6 to about 10 carbon atoms and aromatic hydrocarbons having from about 6 to about 8 carbon atoms. Examples of suitable hydrocarbon extracting agents include hexane, heptane, octane, benzene, toluene, and the like. It is preferable to select a hydrocarbon extracting agent with a relatively low boiling point, in that the hydrocarbon extract phase recovered from the extraction zone is subjected to a distillation to recover the hydrocarbon extracting agent. In this manner, it is possible to minimize the energy requirements necessary for the practice of this invention. For this reason, hexane and benzene are particularly preferred extracting agents.

In the extracting zone, the aqueous 1,4-butanediol-containing mixture is contacted with the extracting agent to effect the extraction of the impurities into the hydrocarbon extract phase. Thereafter, the two phases are separated. This extraction step can be effected by a variety of known methods. For example, a rotating disc contactor may be employed to effect the extraction, alternately, the aqueous butanediol-containing mixture and the extracting agent may be intimately mixed by suitable mixing device and thereafter separated as, for example, by centrifugation or in a suitable settling zone which may include packing material in order to facilitate separation of the phases. A preferred embodiment involves introducing the aqueous 1,4-butanediol-containing mixture at the top of the extraction zone and introducing the extracting agent at the bottom of the extraction zone. The flow of the two streams is countercurrent through the extraction zone wherein they are brought into intimate contact to effect the desired extraction of impurities from the aqueous 1,4-butanediol-containing mixture.

The ratio of hydrocarbon extracting agent to aqueous butanediol-containing mixture will vary depending upon the amount of impurities contained in the aqueous butanediol mixture and the desired degree of removal desired. Generally, a ratio of aqueous 1,4-butanediol to hydrocarbon extracting agent of from about 5:1 to about 1:5 is generally satisfactory, with a ratio of about 2:1 to about 1:2 being preferred. The extraction is carried out in a single extraction phase; however, an alternate embodiment provides for the deployment of a plurality of extraction zones numbering from 2 to about 5. In such extractions involving multiple extractions zones, it is generally preferable to have countercurrent flow of the hydrocarbon extracting agent. Fresh hydrocarbon extracting agent is contacted with the aqueous 1,4-butanediol-containing mixture in the last extraction stage and the recovered hydrocarbon extract phase is then flowed to the preceeding extraction stage, and so forth. It is equivalently useful to employ parallel flow of the hydrocarbon extracting agent, in which the flow of the hydrocarbon extracting agent is divided such that fresh hydrocarbon extracting agent is contacted with the aqueous 1,4-butanediol mixture in each of the extraction stages.

The temperature at which the extraction of impurities from the aqueous butanediol-containing mixture is effected is not critical. The optimum temperature will depend upon the choice of extracting agent and the nature and quantity of the impurities being extracted. Generally, a temperature in the extraction zone of from 25° C. to about 100° C. is generally satisfactory, with a temperature of about 25° C. to about 50° C. being preferred. The pressure at which the extraction zone is operated is generally any pressure at which the two liquid streams are maintained in the liquid state. Pressures of from about atmospheric pressure to 50 psig are adequate for this purpose although higher pressures may be employed if desired.

The hydrocarbon extract phase which is recovered from the extraction zone will generally contain γ-hydroxybutyraldehyde, γ-butyrolactone, butyl fumarate, butyl succinate, butyl butoxy succinate, butoxy-1,4-butanediol and a non-volatile residue. A small proportion of n-butanol may also be present if the initial distillation of the crude hydrogenation zone product is not efficient. This hydrocarbon extract phase is generally subjected to a distillation to recover the hydrocarbon extracting agent for reuse. The extracted impurities substantially free of extracting agent are obtained from the bottom of this distillation zone and may be recycled to the hydrogenation zone wherein these impurities are converted to 1,4-butanediol. However, inasmuch as this bottoms product from the solvent recovery zone will contain a considerable proportion of non-volatile residue, it is preferable to take a slip stream representing a portion of this stream and subject it to further recovery steps to remove the heavy material. Alternately, the distillation of the extract phase may be carried out such that a bottoms product is recovered from the distillation zone which comprises substantially the non-volatile residues and the bulk of the other aforementioned impurities are recovered as a side draw product from a lower portion of the distillation zone.

The raffinate phase recovered from the extraction zone comprises 1,4-butanediol, water and a small proportion of some of the more difficult to remove impurities such as γ-butyrolactone and butoxy-1,4butanediol. This raffinate is introduced to a low pressure distillation zone in which the water is recovered as an overhead product. Any non-volatile residue remaining in the raffinate phase is recovered as a bottoms product from the low pressure distillation zone. 1,4-Butanediol is recovered as a side draw product in high purity and substantially free of water. The pressure at which the low pressure distillation zone is operated should be such that the temperature in the bottom of the distillation zone does not exceed about 150° C. At higher temperatures there is an increased degradation of the 1,4butanediol product which increases the difficulty of obtaining 1,4-butanediol in high purity. The low pressure distillation zone should be operated substantially to exclude the presence of air. Oxygen is known to cause degradation of 1,4-butanediol at elevated temperatures. Therefore, care should be taken in order to ensure that the leakage of air into the low pressure distillation zone is minimized. In an embodiment of this process in which the low pressure distillation is carried out in a batch process, it is preferable to blanket the distillation zone with an inert gas, such as nitrogen.

Figure 1:
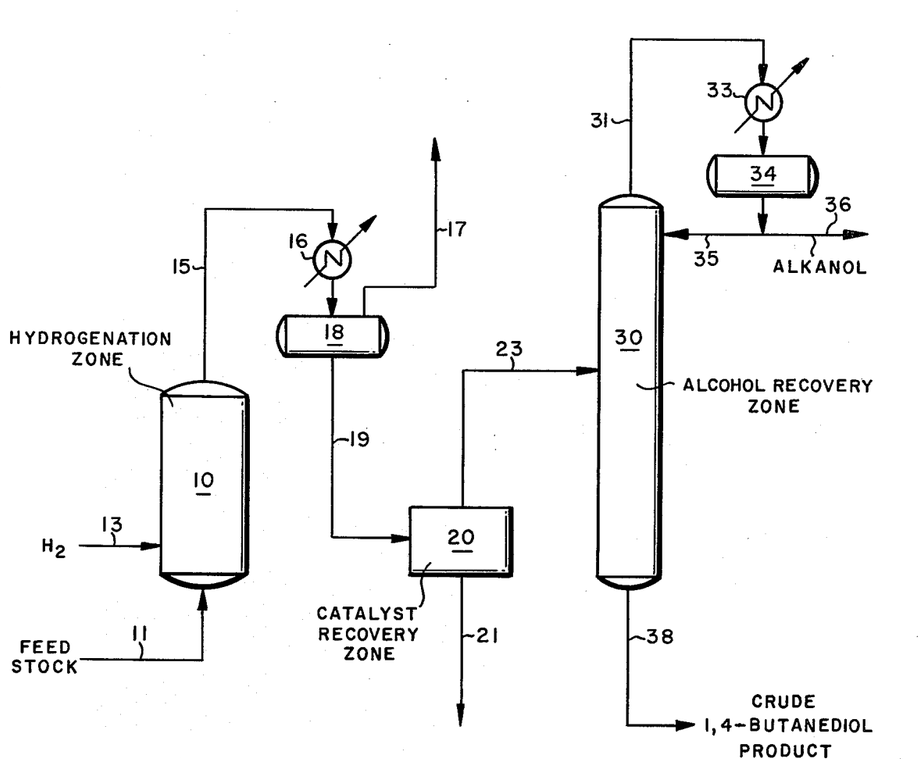

Now reference will be made to the attached FIGURE which represents a schematic flow diagram of a preferred embodiment of the present invention wherein a dibutyl butoxy succinate-containing mixture is converted to 1,4butanediol and n-butanol. It is to be understood that the FIGURE is only a schematic representation of the process and does not purport to show the conventional instrumentation present in a typical process.

A dibutyl butoxy succinate-containing feedstock is introduced into hydrogenation zone 10 via line 11 wherein it is contacted at elevated temperature and pressure with hydrogen in the presence of a copper chromite hydrogenation catalyst. The reactants and catalyst are maintained under vigorous agitation within the hydrogenation zone 10 at a temperature of approximately 250° C. and at a hydrogen pressure of approximately 3,000 psig for a period of approximately 120 minutes. The hydrogen pressure is maintained by the addition of high pressure hydrogen via line 13. The reaction product from the hydrogenation zone 10 comprising 1,4-butanediol and n-butanol is removed from the zone via line 15 and is introduced into heat exchanger 16 wherein it is cooled to a temperature of approximately 30° C. and is allowed to accumulate in a receiver 18. The excess hydrogen gas is vented from receiver 18 via line 17 and is recycled for use in hydrogenation zone 10. The liquid product obtained from receiver 18 is carried via line 19 to a catalyst recovery zone 20 wherein the finely divided copper chromite hydrogenation catalyst is recovered by centrifugation and is recovered from the catalyst recovery zone 20 via line 21. The crude 1,4-butanediol-n-butanol-containing product recovered from catalyst recovery zone 20 is then carried via line 23 to an alcohol recovery zone 30 wherein the crude product is distilled from an overhead product comprising n-butanol. The n-butanol-containing overhead product is carried via line 31 to heat exchanger 33 wherein it is condensed and allowed to accumulate in receiver 34. A portion of this recovered n-butanol is returned via line 35 to the alcohol recovery zone 30 as reflux and the remainder of the crude n-butanol-containing product is recovered via line 36. This n-butanol-containing product may be subjected to further processing steps in order to recover n-butanol in high purity if desired. The bottoms product from the alcohol recovery zone 30 comprises the crude 1,4-butanediol mixture additionally containing impurities and is recovered from alcohol recovery zone 30 via line 38. This crude 1,4-butanediol-containing mixture is typically subjected to further processing steps in order to recover 1,4-butanediol as a high purity "polymer grade" product.

The above invention is characterized in that the process results in the conversion of the dialkyl alkoxy succinate to 1,4-butanediol and the corresponding alkanol(s) all of which are important chemicals of commerce. The 1,4-butanediol is widely used in the production of polybutylene terephthalate and tetrahydrofuran and n-butanol is a commercially important alcohol used as a solvent and as an intermediate in many chemical reactions.

The invention will now be illustrated by the following examples which are for the purposes of illustration and should not be considered a limitation on the scope of the invention.

EXAMPLE 1

A series of runs was made in a stirred autoclave into which was added 200 g. of a crude dibutyl butoxy succinate-containing material having the following composition: 45% dibutyl butoxy succinate and 55% of a mixture of dibutyl maleate and dibutyl fumarate. In each run, 5% by weight of a copper chromite hydrogenation catalyst (No. PC 108–80, Calsicat Division of Mallinckrodt Chemical Works) was added to the autoclave and the autoclave was pressurized with hydrogen and heated to 250° C. In each run, the autoclave contents were intimately admixed by stirring for 1 hour at a particular hydrogen pressure after which the contents of the autoclave were recovered and analyzed for conversion of materials to 1,4-butanediol. In the following Table, the conversion figure refers to the conversion of dibutyl butoxy succinate and the mixture of dibutyl maleate and dibutyl fumarate. The selectivity and yield are for 1,4-butanediol as obtained from both materials.

Table 1

| Run No. | Pressure | Conversion % | Selectivity | Yield |
|---|---|---|---|---|
| 1 | 2,000 | 99 | 92 | 92 |
| 2 | 3,000 | 99 | 92 | 92 |
| 3 | 3,500 | 97.5 | 99 | 97 |
| 4 | 4,000 | 96 | 93 | 90 |

EXAMPLE 2

According to the procedure of Example 1, a number of runs were made wherein the dibutyl butoxy succinate-containing mixture of Example 1 was reduced under 3,000 psig hydrogen pressure but at different temperatures. The copper chromite catalyst concentration in all three runs was 5% by weight based on the reactants. The data are presented in the following Table 2.

Table 2

| Run No. | Temp., °C. | Time (hrs.) | Conversion % | Selectivity | Yield |
|---|---|---|---|---|---|
| 1 | 220 | 1.6 | 99 | 84 | 84 |
| 2 | 250 | 1.5 | 98 | 83 | 80 |
| 3 | 275 | 1.0 | 98 | 93 | 91 |

EXAMPLE 3

According to the general procedure of Example 1, 225.5 g. of a mixture containing 2-butoxy-1,4-butanediol (an intermediate representing the partial hydrogenation of dibutyl butoxy succinate) and dibutyl butoxy succinate were placed in a stirred pressure autoclave with 1.20 g. of copper chromite catalyst and heated to a temperature of 250°–275° C. under 3,000 psig of hydrogen for 1.5 hours. Thereafter, the autoclave contents were recovered and analyzed and the data are presented in the following Table 3. The data indicate that the process of this invention is effective for conversion of 2-butoxy-1,4-butanediol and dibutyl butoxy succinate to 1,4-butanediol in substantially quantitative conversions even when these materials are present only in relatively small amounts with other non-interfering materials.

Table 3

| Compound | Composition, Wt. % | |
|---|---|---|
| | Feedstream | Product |
| n-butanol | 69.5 | 69.9 |
| 1,4-butanediol | 20.0 | 28.2 |
| γ-butyrolactone | — | 1.0 |
| dibutyl succinate | 1.1 | 1.0 |
| 2-butoxy-1,4-butanediol | 5.7 | trace |
| dibutyl butoxy succinate | 3.7 | trace |

EXAMPLE 4

According to the general procedure of Example 1, 279.5 g. of a 2-butoxy-1,4-butanediol-containing mixture was placed in a stirred autoclave along with 15.0 g. of copper chromite catalyst. The autoclave was then heated to 250° C. under 3,000 psig of hydrogen pressure and maintained under these conditions for 1 hour. Thereafter, the autoclave contents were recovered and analyzed for conversion of the 2-butoxy-1,4-butanediol to 1,4-butanediol and n-butanol. The composition of the starting material and the reduced product are presented in the following Table 4. The data demonstrate that approximately 97% of the 2-butoxy-1,4-butanediol was converted to 1,4-butanediol, γ-butyrolactone and n-butanol. The selectivity with respect to each of these compounds is 82.5, 5.2 and 95.0, respectively.

Table 4

| Compound | Composition, wt.% | |
|---|---|---|
| | Feedstream | Product |
| n-butanol | 5.61 | 42.9 |
| γ-butyrolactone | — | 2.53 |
| 1,4-butanediol | 8.78 | 40.29 |
| 2-butoxy-1,4-butanediol | 78.4 | 1.28 |
| non-volatile material | 8.0[a] | 13.0[a] |

[a] The weight percent of the non-volatile material was obtained by difference of the total from 100% and is approximate.

EXAMPLE 5

In a 4 inch dehydrating column equipped with a condenser, 8,967 g. of a crude maleic acid scrubber solution containing 34.8% maleic acid was dehydrated employing xylene as the entraining agent. To the residue in the stillpot was added 5,685 g. of n-butanol and the column was brought to reflux. The distillation column was maintained at reflux for a period of 15.5 hours at a pot temperature of 165° C. A water and n-butanol azeotrope were recovered as an overhead vapor product upon condensation. The water-butanol azeotropic composition was collected in an accumulator and allowed to separate into two layers. The alcohol-rich upper layer was returned to the distillation column as reflux. The acid number of the crude ester contained in the stillpot was measured and found to be 7.1 mg KOH/g. and was not further reduced by additional refluxing for 4.5 hours. The crude product contained approximately 65% by weight of a mixture of dibutyl maleate and dibutyl fumarate and 35% n-butanol.

In a 1 liter autoclave was placed 350 g. of this crude ester product and the autoclave contents were heated to 250° C. under 250 psig pressure. After stirring for 3 hours at this temperature, the autoclave was cooled and the contents were removed from the autoclave. Gas-liquid partition chromatography showed that the product contained 15% dibutyl butoxy succinate, 60% dibutyl fumarate and 25% dibutyl maleate.

In a similar experiment, wherein the crude ester product was placed in the stirred autoclave at 220° C. under 250 psig pressure for 2 hours the product obtained analyzed 31% dibutyl butoxy succinate, 36% dibutyl fumarate and 33% dibutyl maleate.

EXAMPLE 6

In this example, 300 g. of crude 1,4-butanediol was diluted with 300 g. of water and subjected to three extractions employing 200 ml of hexane in each extraction. The composition of the crude 1,4-butanediol and the final purified 1,4-butanediol after the three extractions are presented in the following Table 5. The breakdown of the precent removal of contaminants in each of the three extraction stages is presented for two of the key components, dibutyl succinate and butoxy dibutyl succinate.

Table 5

|  | Crude 1,4-butanediol | Product 1,4-butanediol* |
|---|---|---|
| n-butyl alcohol | 4.39 | Trace |
| γ-butyrolactone | 0.26 | 0.24 |
| 1,4-butanediol | 87.27 | 95.17 |
| γ-hydroxybutyraldehyde | 0.32 | 0.39 |
| dibutyl succinate | 2.62 | Trace |
| 2-butoxy-1,4-butanediol | 4.08 | 4.20 |
| butoxy dibutyl succinate | 0.86 | Trace |

% Ester

Table 5-continued

|  | Removed Per Extraction | | |
|---|---|---|---|
|  | 1st | 2nd | 3rd |
| dibutyl succinate | 89.0 | 10.0 | 0.9 |
| butoxy dibutyl succinate | 90.0 | 9.7 | Trace |

*water excluded from the analysis

The aqueous product 1,4-butanediol obtained from the three extractions was subjected to a low pressure distillation to remove the water. 1,4-butanediol with a purity of approximately 99.7% and uncontaminated with ester was obtained as a final product. In this distillation, 259 g. of the crude 1,4-butanediol were distilled in an 1 inch×33 inch distillation column with an operating pressure of 15–30 mm Hg. A number of cuts were obtained throughout the distillation and analyzed for 1,4-butanediol and impurities. The data are presented in the following Table 6, which data does not include the proportion of water in the overhead cuts. The data indicate that approximately 61% of the crude 1,4-butanediol is recoverable as a high purity 1,4-butanediol product. By comparison, a low pressure distillation was attempted with a crude 1,4-butanediol mixture which had not been subjected to the extraction process of this invention. The data for this distillation are presented in the following Table 7. From an analysis of the data contained therein, it is apparent that approximately only 10% of the 1,4-butanediol contained in the crude diol mixture was recoverable in a purity exceeding 95%.

TABLE 6

Distillation Of Hexane Extracted 1,4-Butanediol

Distribution of Components, Wt.%.

| Cut No. | Wt. g. | Total % Ovhd. | Pot Temp. °C. | n-Butyl Alcohol | unknown | γ-Butyrolactone | 1,4-Butanediol | (γ-Hydroxybutyraldehyde) | Dibutyl Succinate | Dibutyl Fumarate |
|---|---|---|---|---|---|---|---|---|---|---|
| 1 | 15 | 5.8 | 151 | 0.15 | .02 | 1.24 | 95.8 | 2.6 | 0.10 | 0.07 |
| 2 | 17.5 | 12.6 | 151 | 0.03 |  | 0.17 | 98.8 | 1.0 |  |  |
| 3 | 16.0 | 18.8 | 151 | 0.03 |  | 0.44 | 99.3 | 0.5 |  |  |
| 4 | 5.5 | 20.9 | 151 | 0.20 |  | 0.64 | 98.6 | 0.7 |  |  |
| 5 | 14.0 | 26.3 | 153 | 0.10 |  | 0.94 | 98.2 | 0.7 |  |  |
| 6 | 15.0 | 32.1 | 153 | 0.05 |  | 0.24 | 99.5 | 0.4 |  |  |
| 7 | 18.0 | 39.0 | 154 | 0.07 |  | 0.19 | 99.7 | 0.03 |  |  |
| 8 | 15.0 | 44.8 | 155 | 0.05 |  | 0.19 | 99.7 | 0.05 |  |  |
| 9 | 17.0 | 51.4 | 155 | 0.07 |  | 0.22 | 99.7 |  |  |  |
| 10 | 13.0 | 56.4 | 155 | 0.05 | .01 | 0.24 | 99.7 |  |  |  |
| 11 | 12.5 | 61.2 | 155 | 0.06 | .02 | 0.18 | 99.8 |  |  |  |
| 12 | 15.5 | 67.2 | 155 | 0.11 | .11 | 0.56 | 99.2 |  |  |  |
| Undist. Fract. | 85.0 |  |  |  |  |  |  |  |  |  |

TABLE 7

| Cut No. | Wt. g. | H₂O | THF | n-Butyl Alcohol | Dibutyl Formal | γ-Butyrolactone | 1,4-Butanediol | γ-Hydroxy Butyraldehyde | Dibutyl Succinate | Dibutyl Maleate | Butoxy-1,4-butanediol | Butoxy dibutyl Succinate | Unknown |
|---|---|---|---|---|---|---|---|---|---|---|---|---|---|
| 1 | 52.0 | 31.7 | 1.6 | 63.2 | 0.1 |  |  |  |  |  |  |  | 3.4 |
| 2 | 125.0 | 0.9 |  | 98.9 | 0.09 |  |  |  |  |  |  |  | 0.04 |
| 3 | 139.0 | 0.3 |  | 99.7 | 0.03 |  |  |  |  |  |  |  |  |
| 4 | 388.5 |  |  | 99.9 |  |  |  |  |  |  |  |  |  |
| 5 | 13.0 |  |  | 49.1 | 17.2 | 6.4 |  |  |  |  |  |  | 27.3 |
| 6 | 18.0 | 0.2 |  | 3.2 |  | 63.2 | 13.9 | 12.6 |  |  |  |  | 7.0 |
| 7[1)] | 60.9 |  |  | 1.1 |  | 4.2 | 6.1 | 0.6 | 85.3 | 0.2 |  |  | 2.6 |
| 8 | 18.7 |  |  | 3.5 |  | 6.4 | 71.5 | 2.5 | 14.8 | 0.3 | 1.0 |  |  |
| 9 | 26.4 |  |  |  |  | 1.6 | 88.1 | 3.4 | 4.1 | 0.2 | 2.6 |  |  |
| 10 | 25.0 |  |  | 1.5 |  | 1.7 | 84.6 | 0.7 | 1.1 | 0.5 | 9.8 |  |  |
| 11 | 30.5 |  |  | 0.2 |  | 2.2 | 84.5 | 0.8 |  |  | 12.1 |  |  |
| 12 | 36.0 |  |  | 0.3 |  | 0.5 | 91.6 | 0.4 |  |  | 7.2 |  |  |
| 13 | 37.0 |  |  | 0.5 |  | 0.7 | 87.4 | 0.2 |  | 0.2 | 11.4 |  |  |
| 14 | 36.5 |  |  | 0.2 |  | 0.5 | 94.0 | 0.1 |  |  | 5.2 |  |  |
| 15 | 25.7 |  |  | 0.3 |  | 0.4 | 97.1 | trace |  |  | 2.2 |  |  |
| 16 | 22.2 |  |  | 0.6 |  | 0.2 | 98.0 |  |  |  | 1.2 |  |  |

TABLE 7-continued

| Cut No. | Wt. g. | H₂O | THF | n-Butyl Alcohol | Dibutyl Formal | γ-Butyro-lactone | 1,4-Butane-Diol | γ-Hydroxy Butyral-dehyde | Dibutyl Succinate | Dibutyl Maleate | Butoxy-1,4-butane-Diol | Butoxy dibutyl Succinate | Un-known |
|---|---|---|---|---|---|---|---|---|---|---|---|---|---|
| 17 | 34.7 | | | 0.2 | | 0.2 | 99.6 | 0.04 | | | | | |
| 18 | 29.6 | | | 0.3 | | 0.3 | 98.7 | trace | | | 0.4 | | 0.3 |
| Btms Col.[2] | 68.0 | | | | | 0.2 | 19.2 | 0.5 | | | 80.2 | | |
| Hold-up | 15.0 | | | | | | 99.0 | | | | | | |
| Total Wt. | | 18.1 | 0.8 | 693.2 | | 18.6 | 332.6 | 3.1 | 58.4 | 0.4 | 54.6 | 17.1 | |
| Mole% Comp. Excl. of n-Butyl Alcohol and Unk. | | | | | 0.2 | 4.97 | 79.89 | 0.86 | 5.40 | 0.4 | 7.34 | 1.30 | |

[1] Top phase removed from continuous decantor
[2] Composition of column holdup assumed to be 99% diol.

EXAMPLE 7

By a procedure similar to that of Example 6, a crude 1,4-butanediol-containing mixture was subjected to five extractions with equal volumes of benzene. The extraction was done on the crude 1,4-butanediol mixture after removing the n-butanol. The data in the following Table 8 demonstrate that a very high percentage removal of esters are achieved from the crude diol mixture. It is also apparent that benzene is particularly effective in removing γ-hydroxybutyraldehyde and γ-butyrolactone from the crude diol mixture.

Table 8

| | Crude 1,4-butanediol | Raffinate Phase, g. | Extract Phase, g. |
|---|---|---|---|
| 1,4-butanediol | 600.9 | 594.0 | 6.9 |
| γ-hydroxybutyraldehyde | 4.0 | 0.36 | 3.6 |
| γ-butyrolactone | 23.1 | 4.2 | 18.9 |
| butyl fumarate | 45.7 | — | 45.7 |
| butyl succinate | 56.6 | 0.03 | 56.6 |
| butyl butoxy succinate | 34.6 | 0.05 | 34.6 |
| butoxy-1,4-butanediol | 47.0 | 45.8 | 1.2 |
| non-volatile residue | 70.8 | 22.2 | 48.6 |
| | 882.7 | 666.64 | 216.1 |

The high purity 1,4-butanediol product had the following properties:

| | |
|---|---|
| Freeze Point | 20.1° C. |
| Initial Color, Hazen | 10 |
| Water Content (C. Fisher method) | 0.08 |
| After heating 4 hrs. at 190–195° C. | |
| Color | 10 |
| Odor | None |
| Water (C. Fisher) | 0.16 |

We claim as our invention:

1. A process for the production of 1,4-butanediol which comprises intimately contacting dibutyl butoxy succinate with hydrogen in a reaction zone at a temperature in the range of from about 200° C. to about 300° C. and at a hydrogen partial pressure of from about 2,000 psig to about 4,000 psig in the presence of a copper chromite hydrogenation catalyst in an amount of from about 2.0 to about 20.0 wt. %, based on the total reaction mixture, thereby to convert the dibutyl butoxy succinate to a crude reaction mixture comprising 1,4-butanediol and butanol and recovering 1,4-butanediol from the reaction mixture.

2. The process according to claim 1 wherein the copper chromite hydrogenation catalyst is employed in an amount of from about 5 to about 15 wt. %, based on the total reaction mixture.

3. The process according to claim 2 wherein the reaction temperature is in the range of from about 220° C. to about 280° C.

4. The process according to claim 3 wherein the hydrogen partial pressure is from about 2,500 psig to about 3,500 psig.

5. The process according to claim 1 wherein the copper chromite hydrogenation catalyst is recovered from the reaction zone and is recycled for reuse.

* * * * *

UNITED STATES PATENT AND TRADEMARK OFFICE
CERTIFICATE OF CORRECTION

PATENT NO. : 4,172,961

DATED : October 30, 1979

INVENTOR(S) : James D. Henery/Robert P. Arganbright

It is certified that error appears in the above—identified patent and that said Letters Patent is hereby corrected as shown below:

Col. 9, line 55 reads "butoxy-1,4butanediol'' but should read -- butoxy-1,4-butanediol --

Col. 9, line 67 reads "1,4butanediol" but should read -- 1,4-butanediol --

Col. 13, line 30 in Table 5 reads "% Ester" but should be deleted.

Col. 14, line 2 Table 5-continued reads "Removed Per Extraction" but should read -- % Ester Removed Per Extraction --

Signed and Sealed this

Twentieth Day of January 1981

[SEAL]

Attest:

RENE D. TEGTMEYER

Attesting Officer    Acting Commissioner of Patents and Trademarks